United States Patent [19]
Fujioka et al.

[11] Patent Number: 5,171,219
[45] Date of Patent: Dec. 15, 1992

[54] PHARMACEUTICAL PREPARATION ADMINISTRATOR

[75] Inventors: Keiji Fujioka, Amagasaki; Yoshihiro Takada, Suita; Ayumi Aisaka, Moriguchi, all of Japan

[73] Assignee: Sumitomo Pharmaceuticals Co., Ltd., Osaka, Japan

[21] Appl. No.: 534,874

[22] Filed: Jun. 8, 1990

[30] Foreign Application Priority Data

Jun. 8, 1989 [JP] Japan .................. 1-147769
Apr. 20, 1990 [JP] Japan .................. 2-105715

[51] Int. Cl.$^5$ .................. A61M 31/00; A61M 37/00
[52] U.S. Cl. .................. 604/82; 604/85; 604/416; 604/142; 604/90
[58] Field of Search .................. 604/58, 82-85, 604/92, 142, 86-91, 191, 416, 905

[56] References Cited

U.S. PATENT DOCUMENTS

| | | | |
|---|---|---|---|
| 1,381,774 | 6/1921 | Weiner | 604/84 |
| 2,047,437 | 7/1936 | Sinkler | 604/92 X |
| 2,223,611 | 12/1940 | Gross | 604/58 |
| 2,470,293 | 5/1949 | D'Angelo | 604/92 |
| 2,698,015 | 12/1954 | Brown | 604/82 |
| 2,778,360 | 1/1957 | Miskel | 604/90 X |
| 2,798,488 | 7/1957 | Hall | 604/82 |
| 3,337,041 | 8/1967 | Damaskus | 604/92 X |
| 3,354,883 | 11/1967 | Southerland . | |
| 3,682,174 | 8/1972 | Cohen | 604/90 |
| 3,722,500 | 3/1973 | Robinson . | |
| 3,735,900 | 5/1973 | Gores | 604/82 X |
| 3,756,390 | 9/1973 | Abbey et al. | 604/87 X |
| 4,394,863 | 7/1983 | Bartner | 604/191 X |
| 4,479,578 | 10/1984 | Brignola et al. | 604/92 X |
| 4,581,016 | 4/1986 | Gettig | 604/92 X |
| 4,874,381 | 10/1989 | Vetter . | |
| 4,921,142 | 5/1990 | Graf . | |

FOREIGN PATENT DOCUMENTS

| | | | |
|---|---|---|---|
| 519961 | 5/1953 | Belgium . | |
| 0218840 | 8/1986 | European Pat. Off. . | |
| 0311863 | 10/1987 | European Pat. Off. . | |
| 328699 | 2/1988 | European Pat. Off. . | |
| 0282622 | 3/1915 | Fed. Rep. of Germany | 604/82 |
| 0325417 | 9/1920 | Fed. Rep. of Germany | 604/58 |
| 0619625 | 10/1935 | Fed. Rep. of Germany | 604/58 |
| 3704453 | 8/1988 | Fed. Rep. of Germany | 604/82 |
| 1182053 | 6/1959 | France | 604/82 |
| 1493491 | 7/1967 | France . | |
| 2094420 | 2/1972 | France . | |
| 2191912 | 2/1974 | France | 604/82 |
| 0815749 | 7/1959 | United Kingdom | 604/82 |
| 0996168 | 6/1965 | United Kingdom | 604/82 |
| 2211104 | 6/1989 | United Kingdom . | |

*Primary Examiner*—V. Millin
*Assistant Examiner*—Sebastiano Passaniti

[57] ABSTRACT

A preparation administrator has an administrator body including a solid preparation and having at its one end an inflow channel for solvent and at the other end an outflow channel for liquid preparation, a solvent container containing a solvent to dissolve, disperse or suspend the preparation and being connected to the inflow channel of the administrator body, and an ejector for ejecting the solvent together with the solid preparation in the body through the outflow channel of the body. A solid preparation in the administrator body is dissolved, or suspended or dispersed in the solvent fed from the solvent container and ejected as a liquid preparation through the outflow channel of the body.

17 Claims, 6 Drawing Sheets

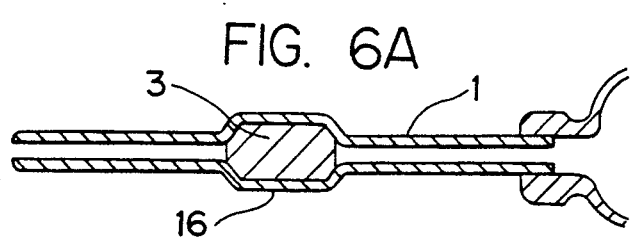
FIG. 6A
FIG. 6B
FIG. 6C
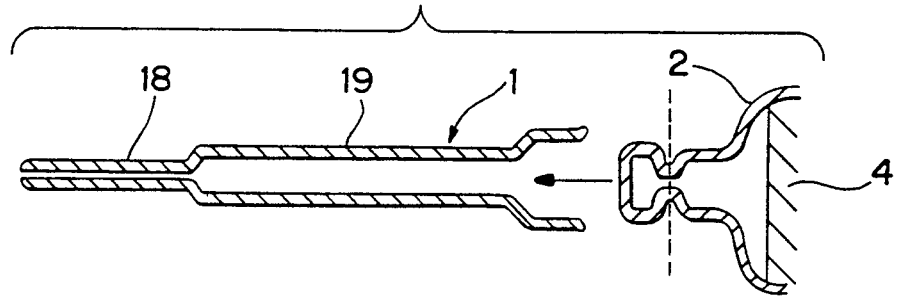
FIG. 6D
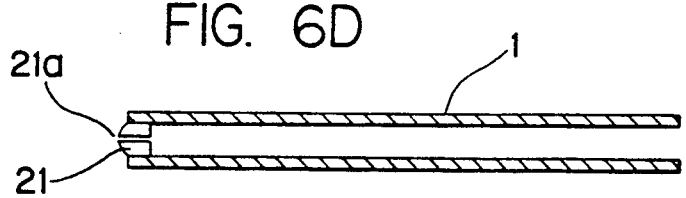
FIG. 6E
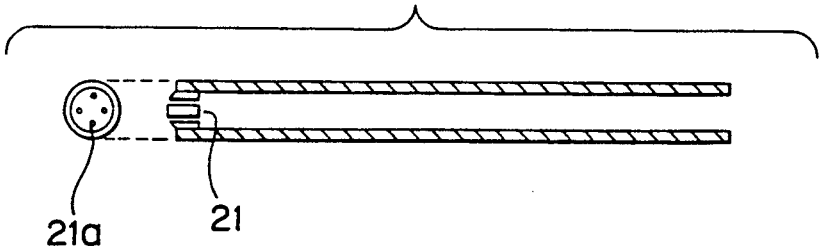

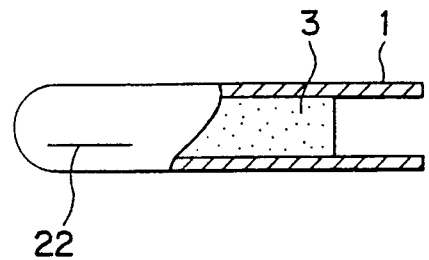
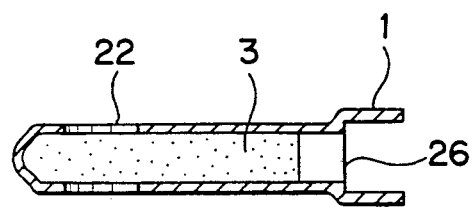
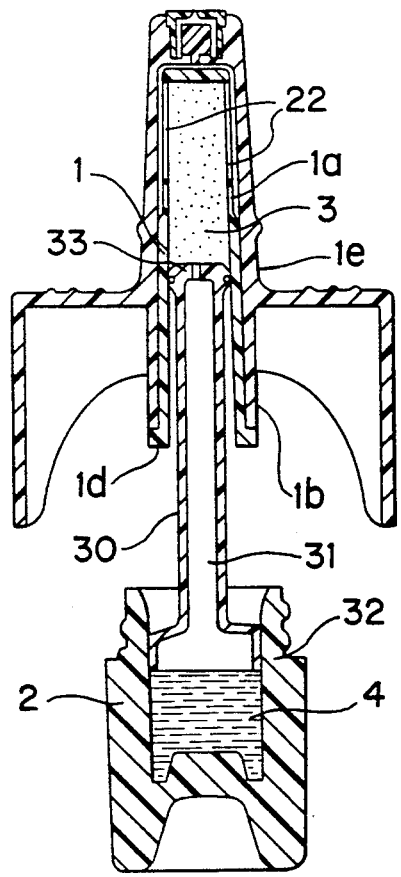

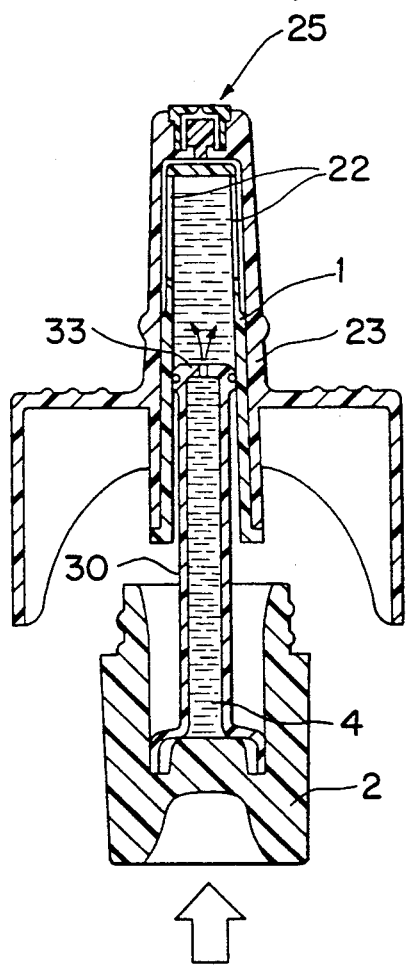
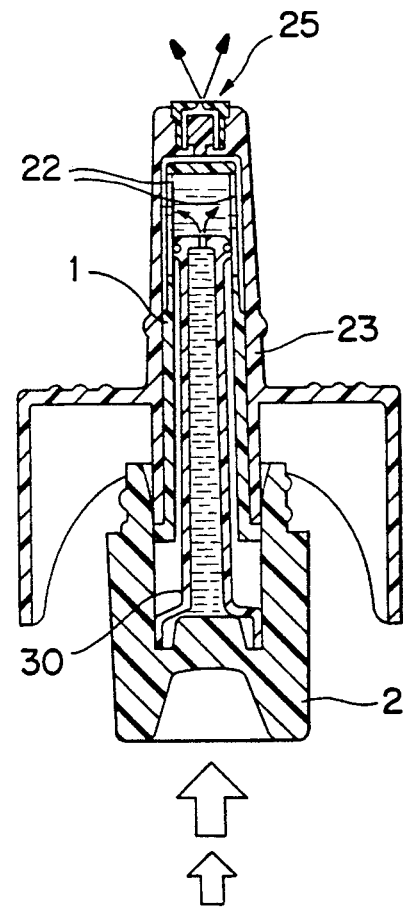
FIG. 11(A)
FIG. 11(B)

PHARMACEUTICAL PREPARATION ADMINISTRATOR

BACKGROUND OF THE INVENTION

1. Field of the Invention

The present invention relates to a pharmaceutical preparation administrator and, more particularly, to a device for administrating one or more solid preparations such as freeze-dried solid preparations along with a solvent as a liquid preparation to nasal or eye mucous membranes.

2. Description of the Prior Art

Recently, peptide materials such as peptide hormones and peptide—or polypeptide—bioactive materials, have attracted the attention of many researchers and induced the great interest in development of medical supplies utilizing such peptide materials as they show great drug efficacy is very small quantities. In order to allow the peptide materials to show the drug efficacy in safe, a certain quantity of the drug has to be absorbed into the body at the administration site. However, the most peptide materials, when orally administered, scarcely show the drug efficacy since they are scarcely absorbed in the gastrointestinal tract and have very low bioavailability because of digestion in the GI tract or of the first pass effect taken place at the liver. In addition, an absorption rate of the peptide materials varies greatly with individuals or with dosing intervals, thus making it considerably difficult to ensure the drug efficacy and safety.

For that reason, it would be necessary to administer peptide preparations by injection to obtain high drug efficacy. The injection ensures the delivery of the drug into the body, but it causes pain to a patient and is inconvenient to operate. Thus, in order to administer preparations frequently and safely, there is an increasing demand for development of administration method which ensures high absorption rate of the drug and which may be replaced for injection.

On the other hand, mucosal applications, for example, intranasal administration, inhalation and eye drop administration, have attracted much interest recently as the drugs are absorbed easily through nasal mucous membranes or eye mucous membranes. Further, the mucous application makes it possible to prevent the drug from inactivation at the GI tract in the digestive canal as well as to avoid the first pass effect at the liver. For the purpose of systematic treatment besides rhinitis and allergic coryza, a certain drug is administered in a liquid preparation intranasally with a suitable administering devices such as, for example, spray, tubes, syringe-type devices.

Taking note of advantages in the mucosal applications, it may be a good idea to administer the aforesaid peptide materials in the form of a solution or a suspension to the mucousal membranes by means of a suitable administering device.

However, peptide hormones and peptide—or polypeptide—bioactive materials are considerably unstable in a liquid state, thus making it very difficult to store them as liquid dosage forms such as solutions, suspensions and dispersions. Thus, the peptide materials must be stored in a dry state to keep their drug efficacy even if it is required to administer such a peptide material in a liquid preparation. If the peptide material is formed into a solid preparation such as a freeze-dried form, the solid preparation must be dissolved, or dispersed, or suspended in a solvent such as distilled water just before use to form a solution, or a suspension, or a dispersion. In addition, the resultant liquid preparation must be charged into a suitable administrating device such as syringes, spray containers, tubes, pipettes and the like to administer it by dropping or spraying. Thus, this method is disadvantageous in that operation is very troublesome and inconvenient.

For injection, it has been proposed to use a syringe comprising a cylinder including powder and a solvent separated by a rubber plug arranged in the cylinder. In use, the solvent is forced to flow into a front powder chamber of the cylinder where the powder contained therein is dissolved in the solvent, and the resultant solution is injected into the human body. Such a pre-filled syringe makes it possible to dissolve the tablet in the solvent by itself, so that there is no need to charge the solution into the syringe. It is, however, impossible to apply such a syringe to administration of peptide preparations as a non-parenteral application because of its structure.

Further, it is difficult with the conventional administrating devices such as spraying devices to administer a very small quantity of the liquid preparation correctly, as well as to administer all the liquid preparation contained therein because of its structure. For that reason, a part of the unused preparation is thrown into the discard together with the administrating device. If such a device is applied to administration of the peptide materials, it is very wasteful as the peptide materials are very expensive. In addition, since the administrating devices of the prior art are designed on condition that they are used repeatedly, there is the possibility of bacteriological contamination of the device during repeated use. In order to avoid the bacteriological contamination, it is required to rinse the administrating device at regular intervals, thus making it very troublesome to handle. In addition, it is difficult with the rinsing operation to sufficiently prevent the administrating device from having bacteriological contamination. To this end, it is obliged to add preservative or antiseptic to the preparation. However, chemicals generally used as the preservative or antiseptic have a strong irritating action for mucous membrane, so that there is the possibility of disturbance of mucous membranes.

SUMMARY OF THE INVENTION

It is therefore a main object of the present invention to provide a preparation administrator which makes it possible to accurately and easily administer a dose of a solid preparation along with a solvent in a liquid preparation to nasal or eye mucous membranes, without causing the loss of expensive preparations.

Another object of the present invention is to provide a preparation administrator which makes it easy to administer a solid preparation as a liquid preparation to nasal or eye mucous membranes by spraying or by dropping.

Still another object of the present invention is to provide a preparation administrator which is fitted for mass production, and which is easy to handle, to operate, and to keep its aseptic condition during storage or transportation.

These and other objects are solved by providing a preparation administrator comprising an administrator body including a solid preparation and having at one end an inflow channel for solvent and at the other end an outflow channel for liquid preparation, a solvent container containing a solvent to dissolve, disperse or suspend said preparation and being connected to the inflow channel of said body, and a means for ejecting said solvent along with said solid preparation through the outflow channel of said body.

According to the present invention, there is also provided a preparation administrator set comprising an administrator body having at either end an inflow channel for solvent and an outflow channel for preparation and including a solid preparation, and a solvent container containing a solvent which dissolves, disperses or suspends said preparation, said administrator body being slidably inserted at one end into said solvent container to constitute a means for ejecting said solvent contained in the container.

Further, there is provided a preparation administrator set comprising an administrator body having at either end an inflow channel for solvent and an outflow channel for preparation and including a solid preparation, a solvent container having a cylindrical chamber containing a solvent which dissolves, disperses or suspends said solid preparation, and a rod-like connector adapted to be slidably inserted at one end into said administrator body and the other end into said solvent container to constitute a means for ejecting said solvent contained in the container.

The administrator body may take any configurations such as, for example, a tubular form, a cylindrical form, a conical form and the like. The body may also have a configuration with different sizes or cross sectional areas for two or more sections. The size of the body may be determined arbitrarily according to the application. For applications to nasal cavities or dropping on the eyes, the administration body is generally made into a tubular member with an outside diameter of 2 to 10 mm, an inside diameter of 1.5 to 9.5 mm, and a length of 10 to 150 mm, preferably, a tubular member with an outside diameter of 2 to 6 mm, an inside diameter of 1.5 to 5.5 mm and a length of 30 to 70 mm.

As a material for the administrator body, there may be used any materials provided that it does not inactivate or denature the pharmaceutical preparation and solvent, and does not cause an interaction between the content and the body. Typical materials for administrator body include, without being limited to, polyethylene, polypropylene, polystyrene, silicone, fluorocarbon polymers, glass. Although these materials may be used alone or in combination, it is preferred to use a transparent or semitransparent elastic material.

The administrator body may be sealed at either end with a thin film to prevent the solid preparation contained therein from absorbing moisture and from being bacteriological contamination. It is preferred to pack the administrator body in an aseptic package to keep it in an aseptic condition until the solid preparation is to be used. If the solid preparation is of an easily oxidizable material, it is preferred to replace the air in the package with nitrogen to improve the drug stability during storage.

The administrator body may be provided at its tip end with a spray nozzle as an integral part thereof. Alternatively, the administrator body may have a spray nozzle adapter removably put on its top or free end. In this case, it is preferred to use an administrator body composed of a hollow member with one end closed in the form of a cylinder, or a conical hollow member, or the like. In this case, the administrator body is provided with at least one outflow channel so designed that it prevents a non-pressurized liquid from passing therethrough, but allows a pressurized liquid to pass therethrough. The outflow channel of the administrator body may be formed in a closed end wall or a barrel of the hollow member close to the closed end thereof. The outflow channel may be formed into any desired shapes such as, for example, in the form of very small circular holes, slit-like incisions, crossed incisions and the like. It is preferred to provide one or more sharp-cut incisions with a length ranging from 1 to 50 mm, preferably, from 1 to 10 mm in the barrel of the hollow member so that they extend in parallel with the axis of the hollow member, although the size of the incisions may vary with the dosage and/or applications.

The nozzle adapter is provided with a bore corresponding to the configuration of the administrator body so that a clearance is formed between the inside wall of the adapter and the administrator body inserted therein to provide a flow channel for the liquid preparation. The flow channel extends from the outflow channel of the administrator body to the spray nozzle provided at the tip of the nozzle adapter. The adapter may be provided at its barrel with a flange or two or more projections extending radially in diametrically opposed directions from each other to permit an operator to hook two fingers around the flanges to allow for easy handling of the administrator. In any cases, the size and shape of spray nozzle may be determined optionally so as to adjust a spraying angle and size and size distribution of particles sprayed.

As a solvent container, any container may be used provided that it contains at least a certain quantity of solvent required for one or more doses of the solid preparation. As a material for the solvent container, there may be used any materials provided that it does not inactivate or denature the solvent and does not cause an interaction between the solvent and container. Typical materials for container include, without being limited to, polyethylene, polypropylene, polystyrene, silicone, fluorocarbon polymers, glasses and the like. These materials may be used alone or in combination.

The solvent container may be formed as an integral part of the administrator body. Alternatively, the container may be formed into a separate member. In this case, the container may be attached to the body, for example, by press-fitting, or by screw mounting or any other connecting means which cause no leakage of the solvent.

The solvent container may comprises a cylinder and plunger slidably arranged therein. In this case, the solvent contained in the cylinder is ejected by inserting the plunger into the cylinder. Thus, the container serves as a solvent ejecting means.

The solvent ejecting means may be formed integrally or separately from the container. Also, the solvent ejecting means may be constituted by the administrator body and the container. If the solvent ejecting means is to be formed as an integral part of the solvent container, the solvent container is formed into a deformable or compressible container with an elastic material such as plastics so that it is easily deformed by pressing its side or bottom wall with fingers to eject the solvent from the container. The solvent ejecting means may be constituted by a piston-cylinder mechanism comprising a cylinder and a piston slidably arranged therein, or by a deformable container with a variable volume.

The solid preparation may be used in any conventionally known forms such as powder, granules and the like. It is, however, preferred to use easily soluble or dispersible solid preparations which may be dissolved, or dispersed or suspended in the solvent only by contacting with the solvent, without performing operation of stirring or heating. The easily soluble or dispersible solid preparations may be formed into powder, granules, membrane, sponge-like form, porous forms. It is preferred to use freeze-dried powder or freeze-dried shaped preparations from the point of view of ensuring the dispersibility or solubility. Because, the preparations produced by a suitable means other than lyophilization is apt to be ejected from the administrator in the solid state as the air, which remains around preparation particles, prevents them from contacting with the solvent. If necessary, the solid preparation may be provided with a through hole to exhaust the air in an air layer formed between the solid preparation and the solvent when the latter is ejected into the bore of the body.

As a material for solid preparations, there may be used any drugs which are unstable or stable in a liquid form. The typical drug includes, without being limited to, peptides, polypeptides and proteins such as hormones, physiologically active materials. Also, the preparation administrator of the present invention may be use for administration of preparations containing one or more drug components which are stable even in a liquid form.

The solid preparation may include one or more additives such as excipients, stabilizers, absorption enhancers, solubilizing agents, suspending agents and the like as occasion demands. Such additives may be selected in accordance with the drug and solvent to be used. For example, if the drug component is a peptide material, for example, a growth hormone releasing factor, it is preferred to use albumin as the stabilizer, as well as to use citric acid or glycine as the solubilizing agent. In that case, the preferred suspending agents are methyl cellulose, polysorbate 80 and the like, while the preferred absorption promoters are saponin, sodium glycocholate, and the like.

The solid preparation may be charged into the administrator body in any ways, for example, by a method comprising the steps of preparing a drug solution, charging the solution containing a dose of drug into a bore of the administrator body, and then lyophylizing the same. Also, the administrators may be produced by charging a dose of powder or granular preparation into the tubular member with one end closed. The powder or granular preparation may be prepared from a drug solution by freeze-drying, spray-drying or any other drying process.

The solvent is selected in accordance with the drug used for solid preparations. Typical solvent used are distilled water, isotonic sodium chloride solution, buffer solutions such as, for example, phosphate buffer solution, citric acid buffer solution, glycine buffer solution.

In use, the administrator body is connected with the solvent container to constitute a preparation administrator, and then the tip end of the administrator body is inserted into a nasal cavity of a patient for example. By operating the solvent ejecting means, the solvent in the container is ejected into the administrator body through the inflow channel of the body so that the solid preparation in the body is immediately dissolved, or suspended, or dispersed in the solvent to form a liquid preparation and then applied to the nasal cavity in the form of droplet or mist through the outflow channel of the body directly or further through the spray nozzle. The preparation administrator makes it possible to administer the preparation in a drop preparation to eye mucous membranes.

According to the present invention, the solid preparation is stored in the administrator body separate from the solvent contained in the solvent container, thus making it possible to store the preparation for a long time even if the preparation is of a peptide material, which is poor in conservation stability in a liquid state, such as peptide hormones, physiologically active materials and the like. Also, all the solid preparation included in the body is administered in a liquid preparation to the nasal cavities or eyes by ejecting part or all of the solvent in the solvent container, thus making it easy to operate. Further, a dose of solid preparation included in the administrator body is dissolved, or dispersed, or suspended in the solvent to form a liquid preparation, and then administered in a liquid form to mucous membranes completely, thus making it possible to ensure administration of the correct dosage of drug as well as to make good use of the solid preparation. Since the administrator body is filled with a dose of preparation, the preparation administrator of the present invention may be used as a disposable. Thus, there is no possibility of bacteriological contamination of the administrator. Also, there is no need to incorporate preservatives or antiseptics, which have a strong irritating action for mucous membranes, into the preparation.

If the administrator body is composed of a hollow member with one end closed and with the outflow channel in the form of one or more very small holes or one or more incisions formed in the closed end wall or side wall of the hollow member so that they prevent a non-pressurized liquid from passing therethrough but allow a pressurized liquid to pass through, it is possible to mass-produce administrator bodies including a solid preparation as there is no possibility of leakage of a liquid through the outflow channel of the body.

The above and other objects, features and advantages of the present invention will be further apparent from the following description taken in conjunction with the accompanying drawings which show, by way of example only, several preferred embodiments of the present invention.

BRIEF EXPLANATION OF THE DRAWINGS

FIGS. 6A-6E are section views showing modified forms of a body of the preparation administrator according to the present invention;

FIGS. 9A and 9B are section views showing a modified form of a preparation administrator according to the present invention;

FIG. 10 is a section view of a preparation administrator showing another embodiment of the present invention; and FIGS. 11A and 11B are section views of a preparation administrator of FIG. 10 in operation.

PREFERRED EMBODIMENTS OF THE INVENTION

Figure 1:
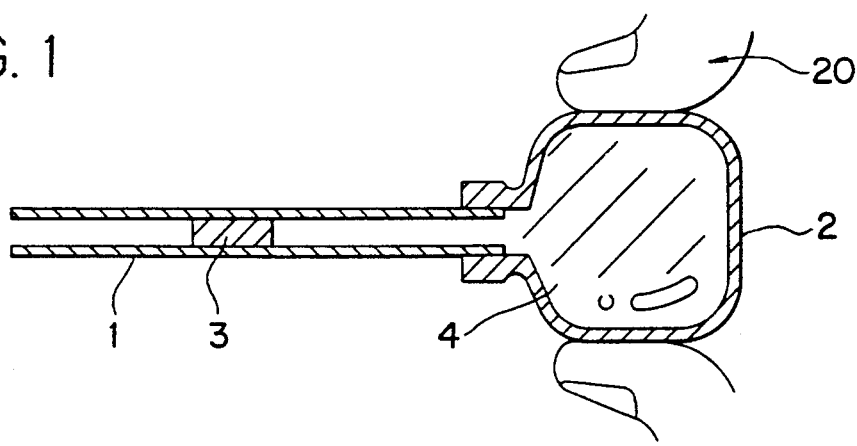
FIG. 1 is a section view of a preparation administrator embodying the present invention.

FIG. 1 shows a preparation administrator embodying the present invention, comprising a tubular administrator body 1 having an inflow channel for solvent and an outflow channel for liquid preparation and including a solid preparation 3 charged in its bore. The body 1 is inserted at its one end into a deformable solvent container 2 filled with a certain quantity of a solvent. The container 2 is made up of a flexible material or of a soft material so that it is deformed easily by applying a force to constitute a solvent ejecting means.

Before assembly, the administrator body 1 is provided on both ends with thin films to hermetically seal both the ends of its bore, while the solvent container 2 is closed by a cap (not shown). Also, the body and container 2 are packed in an aseptic package to ensure the asepsis of the preparation administrator during storage and transportation.

In use, the body 1 and container 2 are firstly unpacked and then joined together by inserting the one end of the body into the mouth of the container 2 to make the preparation administrator ready for use, as shown in FIG. 1. After inserting the tip end of the body 1 into the nasal cavity or after positioning the tip end of the body 1 just above the eye, the container 2 is deformed by pressing its side wall by fingers 20, as illustrated in FIG. 1, to supply the solvent 4 to the bore of the body 1. The solid preparation 3 in the body 1 is dissolved, or dispersed or suspended in the solvent 4 to form a solution, or a dispersion or a suspension, and administered to the nasal cavity or eyes through the outflow channel of the body 1.

Figure 2:
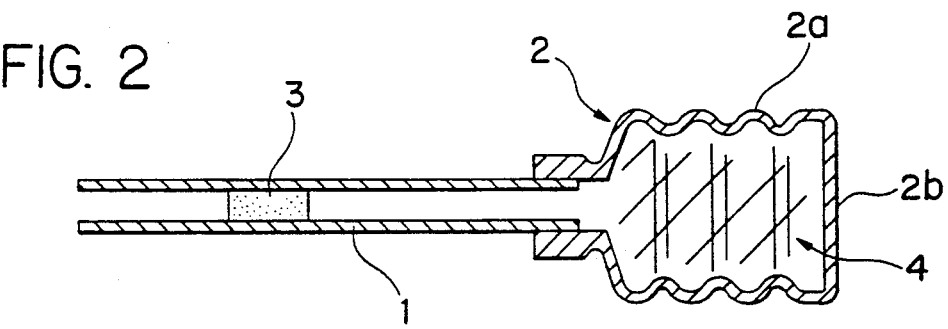
FIG. 2 is a section view of a preparation administrator showing another embodiment of the present invention.

In another preferred embodiment of the preparation administrator shown in FIG. 2, a barrel 2a of the solvent container 2 is formed into a bellows form so that it may expand and contract in the direction parallel to its axis. The container is deformed easily by pressing its bottom to supply the solvent 4 contained therein to the administrator body 1. In use, the body 1 is screwed in the mouth of the container 2, as shown in FIG. 2.

For the preparation administrators in the foregoing embodiments, it is preferred to pair the body containing a dose of a solid preparation with the solvent container filled with a solvent more than the required amount for a dose of the solid preparation to allow these parts to be disposable. In that case, whole or a part of the solvent is used to administer the dose of the solid preparation. However, the solvent container may be used for several times in combination with several administrator bodies, provided that the administrator body is replaced with a new one every time the administration is performed. This may be achieved, for example, by use of a solvent container as shown in FIG. 3.

Figure 3:
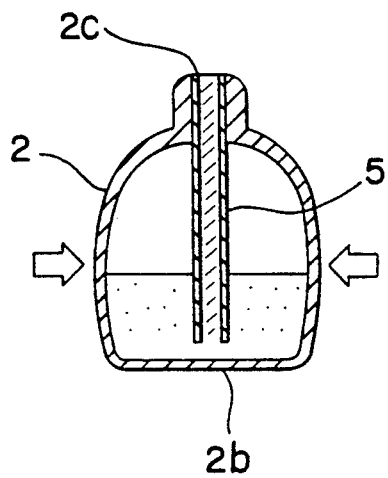
FIG. 3 is a section view showing a modification of the preparation administrator of FIG. 1.

In the embodiment of FIG. 3, the deformable solvent container 2 is provided with a pumping tube 5 inserted into the container 2 through its mouth 2c so as to extend close to its bottom 2b. The container 2 is used in combination with a tubular administrator body 1 with a hub, as shown in FIG. 6C.

In use, the body is attached to the top of the container 2 and then the container is pressed slightly to fill the pumping tube 5 with the required amount of the solvent for a dose, while keeping the container right end up. Then, the container is turned upside down, and further pressed to supply the solvent in the pumping tube 5 to the administrator body. The solvent dissolves the solid preparation in the body, thus making it possible to administer the solid preparation as the liquid preparation. After removing the body from the container, a cap is put on the solid container to store it for next use.

In that manner, the solvent container may be used several times in combination with several administrator bodies each containing a dose of preparation, provided that the solvent container is filled with a solvent several times the required quantity for a dose. It is unnecessary to turn the solvent container upside down during administration of the preparation.

Figure 4:
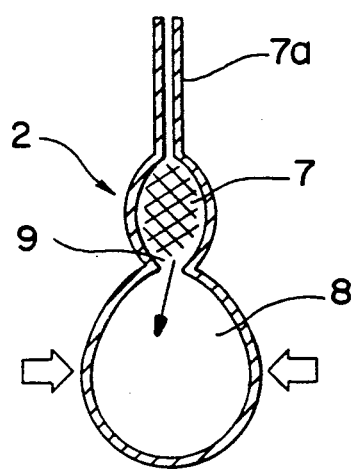
FIG. 4 is a section view of a preparation administrator showing another embodiment of the present invention.

In another embodiment shown in FIG. 4, a preparation administrator comprises a solvent container 2 formed in a gourd shape to form two chambers, i.e., a solvent chamber 7 filled with a dose of a solvent, and a gas chamber 8 charged with air or any gases. The gas chamber 8 is communicated with solvent chamber 7 through a narrow passage 9 at a compressed part of the container. By pressing the gas chamber to reduce its capacity, the gas in the gas chamber 8 is fed to the solvent chamber 7 so that the solvent in the solvent chamber 7 is ejected through a tubular portion 7a on which a tubular administrator body with a dose of preparation is attached.

It the solvent chamber 7 is communicated with the gas chamber 8 by a passage 9 with a relatively large sectional area, the passage 9 may allow the solvent in the chamber 7 to flow into the gas chamber. In such a case, it is sufficient to turn the container upside down before using to return the solvent in the gas chamber 8 to its original chamber 7.

Referring now to FIG. 5, there is shown a preparation administrator embodying the present invention, which comprises a tubular administrator body 1, a tubular solvent container 2, and a solvent ejecting means 10 to be connected to the container 2. The tubular body 1 includes a dose of an easily soluble solid preparation 3 arranged in its bore, and is covered at both ends with a sealing membrane 11. The container 2 is filled with a dose of a solvent 4 and covered at both ends with a sealing membrane 12. The solvent ejecting means 10 has a construction similar to that of a well-known syringe and consists of a cylinder 13 and a piston rod 14 slidably arranged in the cylinder 13.

Figure 5A:
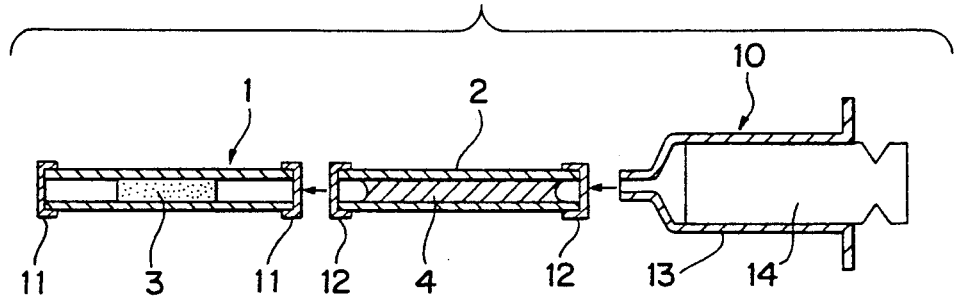
FIGS. 5A-5E are section views of a preparation administrator showing another embodiment of the present invention in operation.
Figure 5B:
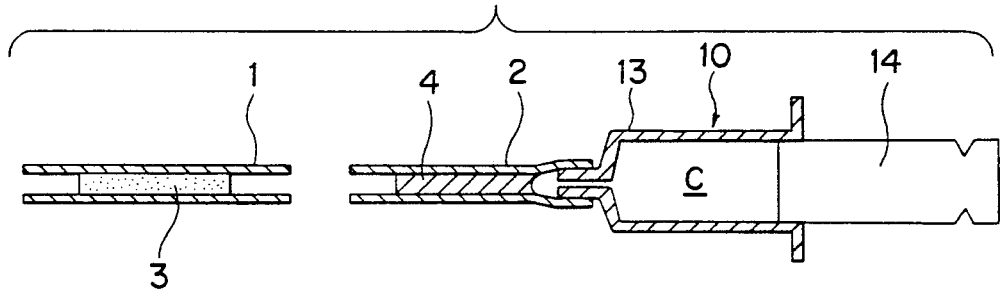
Figure 5C:
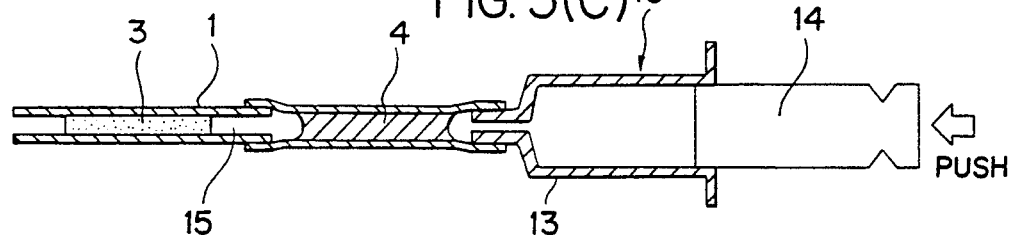

In use, the administrator is firstly made ready for use in the following manner. The piston rod 14 of the solvent ejecting means 10 is moved from the position shown in FIG. 5A to a position shown in FIG. 5B. After removing the sealing membranes 11 and 12 from the body 1 and container 2, the container 2 is connected to the solvent ejecting means 10 by inserting the tip of the cylinder 13 into its one end (FIG. 5B), and then to the administrator body 1 by inserting one end of the body 1 into the opposite end of the container (FIG. 5C).

Figure 5D:
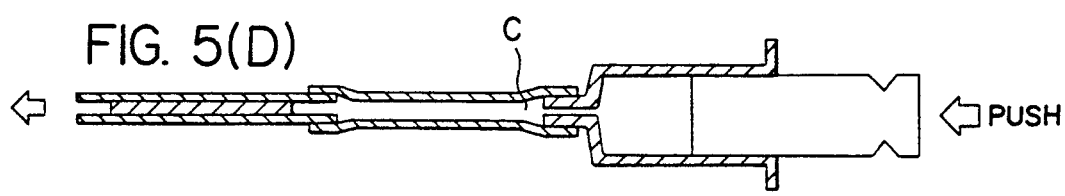
Figure 5E:
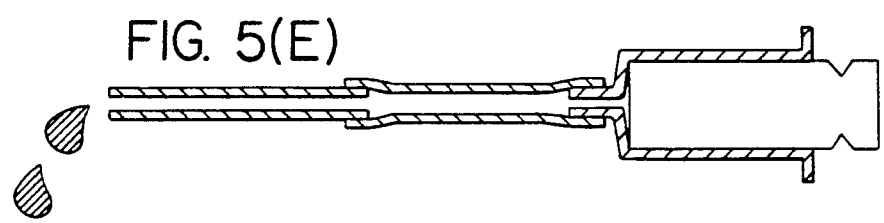

Next, the administrator is positioned at the administration site, for example, by inserting the tip end of the body in the nasal cavity, and the piston rod 14 is pressed in the cylinder 13 so that the solvent 4 in the container 2 is ejected therefrom and fed to the solid preparation 3, as shown in FIG. 5D. In that case, the air in the space between the solid preparation 3 and the solvent 4 may be released out of the body through very small holes of the solid preparation 3, as illustrated by an arrow in FIG. 5D, provided that the solid preparation is of a porous or sponge-like structure. Thus, there is no fear of causing undesirable phenomenon such that the solid preparation is pushed out as it is. In contact with the solvent, the solid preparation is dissolved, or dispersed, or suspended in the solvent to form a liquid preparation such as, for example, a solution, a dispersion, or a suspension. The resultant liquid preparation is administered to the nasal cavity through the outflow channel of the administrator body 1 by further pushing the piston rod 14 into the cylinder 13.

In all the foregoing embodiments, a straight tubular member is used for the administrator body, but there is no restriction in shapes of the administrator body. The administrator body may take any desired the shape as occasion demands. For example, as shown in FIG. 6, there may be used any administrator bodies such as those having at the central part a large-sized portion 16 with a solid preparation 3 charged therein (FIG. 6A), or those having at the front part a tapered portion 17 (FIG. 6B), or those including a small-sized tubular portion 18 and a large-sized tubular portion 19 integrally formed therewith to contain a solid preparation (FIG. 6C), or those having at the tip a spray nozzle member 21 with one or more orifices 21a (FIGS. 6D, 6E). The administrator body 1 shown in FIG. 6C may be used in combination with a solvent container 2 having a closed top formed as an integral part of the container. In that case, the container 2 is cut along a broken line shown in the figure to remove the top, and then inserted at the cut portion into the inflow channel of the body 1.

Further, the administrator in the foregoing embodiments is composed of two separate members, i.e., an administrator body and a solvent container, but these members are formed integrally. For example, the preparation administrator may be constructed by a gourd-shaped solvent container as shown of FIG. 4. In this case, a tubular portion extending from the solvent chamber is used as the administrator body and charged with a solid preparation. The solid preparation and the solvent are separated by a partitioning member such as a thin film or a membrane to prevent the solid preparation from contact with the solvent in the solvent chamber. In use, the partitioning member may be broken by compressing the gas chamber 8 to increase its internal pressure, or by thrusting a sterilized needle member in the partitioning member through the bore of the tubular portion.

In the foregoing embodiments, the administrator body is composed of a tubular member or a conical hollow member opened at both ends. For this reason, there are some problems awaiting a solution. For example, since the administrator body is opened at the both ends, it is considerably difficult to charge a preparation into the body held in the vertical position like general containers. In addition, the preparation has to be positioned in the middle part of the bore of the body. For that reason, it is required to put the preparation into the body held in the horizontal position, thus making it difficult to produce. Further, since the preparation in the bore of the body is unstable in position, there is a fear of the preparation falling from the body through its openings. Thus, handling of the body requires sufficient care.

A solution to these problems is to close one end of the administrator body with a plug or to seal one end of the administrating member. However, it requires an additional operation such as removal of the plug or cutting operation of the sealed end to make the administrator body ready for use. In addition, it is troublesome to plug up a bore of a small-sized administrator body as well as to pull out the plug. Also, it is feared that the preparation stuck to the plug may spill out when pulling out the plug. These problems in the production and operation of the above administrators are solved by the embodiment of FIG. 7.

Figure 7:
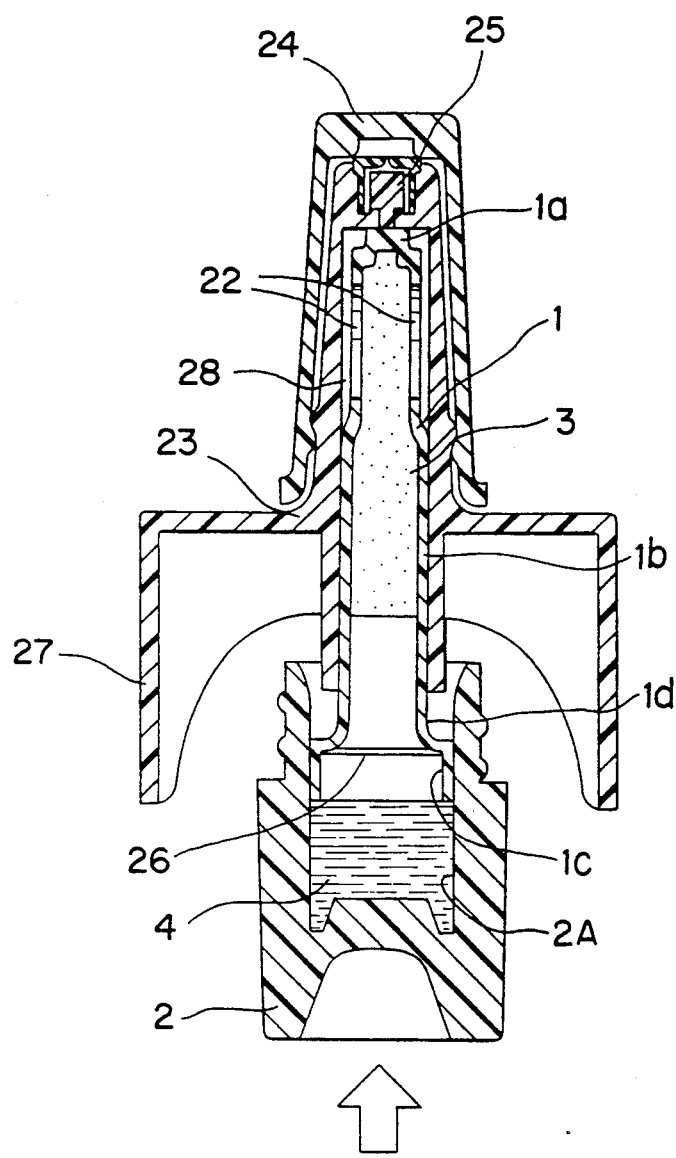
FIG. 7 is a section view of a preparation administrator showing another embodiment of the present invention.
Figure 8:
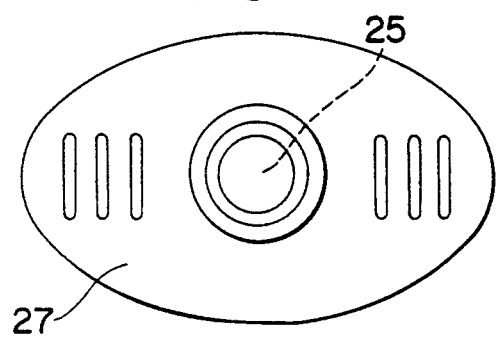
FIG. 8 is a plane view of the preparation administrator of FIG. 7.

Referring now to FIG. 7, there is shown a preparation administrator set comprising a cylindrical administrator body 1, a cylindrical solvent container 2 and a spray nozzle adapter 23 into which the administrator body 1 is inserted. A hood 24 is put on the top of the nozzle adapter to protect the same.

The administrator body 1 is a top-closed cylindrical member with different sizes for the front, middle and rear. A front portion or barrel 1a with a tip end closed is provided at its side wall with two slit-like clean-cut incisions 22 each of which extends in parallel with the center axis of the body and serves as an outflow channel for the liquid preparation. The body 1 is so designed that the outside diameter of the front barrel 1a is smaller than that of the middle barrel 1b, while the outside diameter of a rear barrel 1c is greater than that of the middle barrel 1b but equal to or smaller than the inside diameter of the container 2. The administrator body 1 is charged with a dose of a solid preparation 3 and provided with an easily soluble membrane 26 at a stepped portion 1d between the middle and rear barrels 1b and 1c.

The solvent container 2 is a bottom-closed cylindrical member and is provided with a cylindrical chamber 2A so that the rear barrel 1c of the administrator body 1 may fit in the chamber 2A and slide longitudinally to eject a solvent 4 contained in the chamber 2A. Before assembly of the administrator set, a cap (not shown) is screwed on a threaded tubular extension of the container 2 filled with a certain amount of the solvent.

The spray nozzle adapter 23 is a cylindrical member with a bore having an inside diameter equal to the outside diameter of the middle barrel 1b. The nozzle adapter 23 is provided at its tip with a spray nozzle tip 25. At the side wall close to the rear end there is provided an elliptical flange 27 to allow the operator to hook fingers around the flange 27 to allow for easy operation of the administrator. Between the inner wall of the nozzle adapter 23 and the front barrel 1a of the body, there is formed a circular gap 28 serving as a passage extending from the outflow channel 22 of the administrator body 1 to the spray nozzle 25.

The administrator body 1 with a dose of solid preparation may be produced, for example, by a method comprising the steps of molding a suitable plastic material into tubular members with one end closed, forming one or more incisions in a barrel of tubular member, holding the tubular members in the vertical position, charging a dose of a preparation into a bore of each tubular member, and then closing the open end of each tubular member with an easily soluble membrane 26 such as a gelatine film or a medicinal wafer, which prevents the preparation from scattering or falling out during production or transportation.

In that case, the preparation may be used in any desired forms such as powder, granules or a liquid. If the preparation is used in the form of a liquid, the liquid preparation charged is freeze-dried before closing the open end of the tubular member with the membrane 26. In this case, there is no leakage of the liquid preparation in the administrator body 1 during its production as the cut surfaces of the incision 26 are brought in close contact because of the elasticity and physical structure of the body. Thus, the preparation administrator in this embodiment can be mass-produced in simple operation and improved in shelf stability.

The easily soluble membrane 26 may be replaced with a lid or any desired porous materials such as, for example, sponges, reticulated films, disks with slits and the like. Also, the porous material may be inserted in the bore of the administrator body 1 before closing the open end with the easily soluble membrane.

In use, after removing the hood 24 from the administrator set, the nozzle adapter 23 is held, for example, with the middle and index fingers so as to hook these fingers around the flange 27 and then the container 2 is pushed slowly by the thumb to allow the container 2 to slide along the rear barrel 1c of the administrator body 1. With increase in the stroke of the container 2, the solvent 4 contained therein is applied the pressure and flows into the administrator body 1 where the solid preparation 3 is dissolved, or dispersed or suspended in the solvent to form a liquid preparation. The resultant liquid preparation in the body 1 is forced into the passage between the body 1 and nozzle adapter 23 by forcing the incisions 22 open, and then sprayed through the nozzle tip 24 of the adapter. Thus, the preparation administrator is easy to operate.

In the embodiment of FIG. 7, the administrator body 1 is formed in the form of a tubular member with different sizes for three sections, but it may take any configurations as shown in FIG. 9.

Referring first to FIG. 9A, an administrator body 1 is composed of a tubular member with one end closed, and its outside diameter is uniform over all the length. At the front part of the tubular member, there are two sharp-cut incisions 22 extending in the direction parallel to the axis of the body 1 and serving as the outflow channel for liquid preparation. The incisions may be formed radially along the side wall of the administrator body 1. Also, the incisions may be formed in the closed end wall of the administrator body. In all cases, the incision may be formed in a crossed shape or any desired shapes.

FIG. 9B shows another form of an administrator body comprising a tubular member with a configuration similar to that of FIG. 9A except for that it has a large-sized rear portion. The large-sized rear portion is so designed that it may fit in the bore of the solid container and slides along the inner wall of the bore.

In the embodiment of FIG. 7, the preparation administrator set includes the spray nozzle adapter 23. However, there is no need to use nozzle adapter 23 as part of the administration set. In such a case, the administrator set is composed of an administrator body including a dose of solid preparation charged therein, and a solvent container filled with a certain quantity of a solvent for a dose of preparation. The administrator body and the container may have configurations similar to those of FIG. 7. Thus, the solid preparation and the solvent form a liquid preparation in the administrator body, and the liquid preparation is ejected directly through the incisions of the administrator body. In this case, it is preferred to provide a flange similar to that of the nozzle adapter 23 or projections extending radially in diametrically opposed directions from each other to permit the operator to hook fingers around the flange or projections to allow for easy handling of the administrator set.

FIG. 10 shows another embodiment of a preparation administrator set having a structure similar to that of the embodiment of FIG. 7 except for the following points. The administrator set includes a rod-like connector 30 in addition to an administrator body 1 and a solvent container 2. The administrator body 1 is composed of a tubular member with different sizes for the front and rear. The front half 1a of the body 1 is closed at tip end and provided at its side wall close to the tip end with two slit-like incisions 22 to form outflow channels for the liquid preparation. The rear half 1b of the body 1 is provided at its rear end with an outwardly extending flange 1d, and at a middle portion of its bore with a projection 1e serving as a stopper for the connector 30.

The solvent container 2 is composed of a cylindrical member with one end closed and has a cylindrical solvent chamber which is filled with a certain quantity of a solvent. An inlet portion of the solvent chamber is formed in the shape of an unfolded fan to facilitate insertion of the connector 30.

The rod-like connector 30 has a bore passing therethrough and is provided at its one end with a cylindrical head 32 having an outside diameter substantially equal to the inside diameter of the container 2, and at the other end with a disk-like piston head 33 having an outside diameter substantially equal to the inside diameter of the administrator body 1. Thus, the cylindrical head 32 can slide within the chamber of the container 2, while the disk-like piston head 33 can slide within the bore of the administrator body 1. The disk-like piston head 33 is provided at its center with a hole to allow the solvent in the connector 30 to flow into the administrator body 1.

In use, after making the preparation administrator set ready for use, as shown in FIG. 10, the container 2 is forced upwardly in the figure. At that time, the piston head 33 is in contact with the projection 1e in the bore of the administrator body 1 and is stopped, so that the container 2 is moved along the cylindrical head 32 of the connector 30. For that reason, the solvent 4 flows into the connector 30 and then into the administrator body 1 where the solid preparation is dissolved in the solvent to form a liquid preparation, as shown in FIG. 11A. Further forcing the container 2 upwardly, the piston head 33 passes through the projection 1e and ejects the solvent from the body 1 through the incisions 22, so that the liquid preparation is sprayed by the spray nozzle 25 as shown in FIG. 11B.

According to the present invention, the preparation can be stored aseptically in a dry state, thus making it possible to store the preparation for a long period of time even if the preparation contains a peptide material which is unstable in a liquid state, such as peptide hormones, physiologically active materials and the like. In addition, it is easy to make the administrator set ready for use. It is also possible to administer a dose of solid preparation to nasal mucous membranes or eye mucous membranes in the form of a liquid preparation with ease as the solid preparation is dissolved, or dispersed or suspended in the solvent in the course of the administrating operation.

EXAMPLE 1

There were prepared administrator bodies as shown in FIG. 7 by molding polyethylene with a metal mold into tubular members with one end closed, and then making two sharp-cut incisions in a side wall of each tubular member with a sharp knife.

Separate from the above, there was prepared an aqueous solution containing 0.5 g of glycine in a mixed solution of 1 ml of 25% human serum albumin and 49 ml of purified water. The resultant aqueous solution was adjusted to about pH 5 with hydrochloric acid. Powder of 5 mg of growth hormone releasing factor (GRF) was dissolved in 1 ml of the resultant aqueous solution, and filtered through a membrane filter to prepare a liquid preparation for test samples.

The resultant liquid preparation (100 µl) was charged into the above administrator body with a micropipette, and then freeze-dried in the conventional manner to prepare a solid preparation charged in the administrator body.

The thus prepared administrator body 1 was loaded as a preparation cartridge into a previously prepared spray nozzle adapter 23 shown in FIG. 7, and then inserted in the top and let it go several millimeters into a previously prepared solvent container 2 containing 300 µl of purified water to make the administrator ready for use.

When the container 2 was pushed against the adapter 23, the purified water 4 in the container 2 was fed to the administrator body 1, and then ejected in the mist through the spray nozzle of the adapter 23. The solid preparation was not observed in the administrator body. Accordingly, it will be understood that the freeze-dried GRF solid preparation dissolves in the solvent instantly and is administered as a liquid preparation by spraying.

EXAMPLE 2

There was prepared an aqueous solution containing 1 g of glycine and 2.5 g of mannitol in a mixed solution of 2 ml of 25% human serum albumin and 98 ml of purified water, which was then adjusted to about pH 5 with hydrochloric acid. Powder of 10 mg of GRF was dissolved in 1 ml of the resultant aqueous solution, and then filtered through a membrane filter to prepare a liquid preparation for the sample.

The resultant liquid preparation (100 µl) was charged into the administrator body prepared in Example 1, and then freeze-dried to prepare an administrator body including a dose of solid preparation, as shown in FIG. 7.

The thus prepared administrator body 1 was loaded into the spray nozzle adapter 23, and then inserted in the top and let it go several millimeters into a solvent container 2 containing 300 µl of purified water to make the administrator ready for use.

By pushing the container 2 against the adapter 23, spray administration was easily achieved in the same manner as Example 1. It was observed that there was no solid preparation remained in the administrator body. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A preparation administrator for spraying a liquid preparation to mucous membranes comprising:
    a tubular member closed at one end but open at the other end, said tubular member containing a dose of a solid preparation and being provided with at least one outflow channel, the outflow channel preventing a non-pressurized liquid from passing therethrough but allowing a pressurized liquid to pass therethrough;
    means for spraying a liquid preparation, said spraying means being provided on said tubular member to form a circular clearance therebetween and in communication with the outflow channel of said tubular member through said clearance; and
    a solvent container having a bottom-closed cylindrical member, the container containing a solvent for said solid preparation, said container being connected to said tubular member to constitute a means for ejecting said solvent into said tubular member through the open end thereof to thereby form a liquid preparation just before use and then to spray the resultant liquid preparation to mucous membranes through said spraying means.

2. The preparation administrator according to claim 1, wherein said outflow channel is constituted by at least one incision formed in the side wall of said tubular body.

3. The preparation administrator according to claim 1, wherein said outflow channel is constituted by a generally straight and narrow incision cut in the side wall of said tubular member.

4. The preparation administrator according to claim 1, wherein said outflow channel is a very small hole formed in the closed end wall of said tubular member.

5. The preparation administrator according to claim 1, wherein said solvent container has a cylindrical chamber containing said solvent into which said tubular member is slidably inserted to constitute said solvent ejecting means.

6. The preparation administrator according to claim 1, wherein said solid preparation is easily soluble in said solvent.

7. The preparation administrator according to claim 1, wherein said spraying means comprises a spray nozzle formed as an integral part of said tubular member.

8. The preparation administrator according to claim 1, wherein said solid preparation is a freeze-dried peptide material.

9. The preparation administrator body according to claim 1, wherein said circular clearance is formed between the inside wall of the spraying means and the outside wall of the tubular member inserted therein.

10. The preparation administrator according to claim 1, further comprising a generally straight, slender, cylindrically shaped connector, said connector being slidably arranged at one end in said solvent container with a cylindrical chamber, and at the other end in said tubular member to constitute said solvent ejection means.

11. The projection administrator according to claim 10, wherein said tubular member has a projection formed at a middle portion thereof, the projection being engageable with the connector and the projection temporarily stopping sliding of the projection during administration.

12. The preparation administrator according to claim 1, wherein said spraying means comprises a cylindrical spray nozzle adapter provided at one end with a spray nozzle tip and at the other end with a bore for attachment of said tubular member, and wherein said tubular member is fitted in the bore of said nozzle adapter to form a passage through which the outflow channel of said tubular member is communicated with said nozzle tip.

13. The preparation administrator according to claim 12, wherein said spray nozzle adapter is provided at one other end thereof with a cylindrical flange.

14. The preparation administrator according to claim 12, wherein said tubular member has an outside diameter uniform over an entire length thereof and substantially equal to an inside diameter of the solvent container, said tubular member being closed at one end and being provided at a side wall close to said closed end with at least one incision to form said outflow channel.

15. The preparation administrator according to claim 12, wherein said tubular member has a small-sized front portion closed at one end, and a large-sized rear portion adapted to be fitted in said solvent container, said front portion being provided at a side wall near the closed end with at least one incision to form said outflow channel.

16. The preparation administrator according to claim 12, wherein said tubular member has different sizes for three sections, the front section having an outside diameter smaller than that of the middle section, while the rear section having an outside diameter greater than that of the middle section but substantially equal to an inside diameter of the solvent container, said front section being closed at a tip thereof and being provided with said outflow channel.

17. The preparation administrator according to claim 16, wherein the middle section of said tubular member has an outside diameter substantially equal to the inside diameter of the bore of said nozzle adapter.

* * * * *